(12) United States Patent
Amitai et al.

(10) Patent No.: US 6,625,545 B1
(45) Date of Patent: Sep. 23, 2003

(54) METHOD AND APPARATUS FOR MRNA ASSEMBLY

(75) Inventors: Mor Amitai, Tel Aviv (IL); Raveh Avraham Gill-More, Rosh Ha'ayin (IL); Eran Halperin, Tel Aviv (IL); Avner Magen, Jerusalem (IL); Sarah Rachel Pollock, Tel Aviv (IL)

(73) Assignee: Compugen Ltd., Tel Aviv (IL)

(*) Notice: Subject to any disclaimer, the term of this patent is extended or adjusted under 35 U.S.C. 154(b) by 0 days.

(21) Appl. No.: 09/133,987

(22) Filed: Aug. 13, 1998

(30) Foreign Application Priority Data

Sep. 21, 1997 (IL) .................................................. 121806

(51) Int. Cl.⁷ .......................... G06F 19/00; C12Q 1/68; C12N 15/11
(52) U.S. Cl. ............................... 702/19; 702/20; 435/6; 536/23.1
(58) Field of Search .............................. 702/19, 20, 21; 435/6, 91.2; 536/23.1

(56) References Cited

U.S. PATENT DOCUMENTS 6,189,013 B1 * 2/2001 Maslyn et al.
6,223,186 B1 * 4/2001 Rigault et al.

OTHER PUBLICATIONS

Rounsley et al. The Construction of Arabidopsis Expressed Sequence Tag Assemblies. Plant Physiology vol. 112, pp. 1177 1183 (1996).*

* cited by examiner

Primary Examiner—John S. Brusca
(74) Attorney, Agent, or Firm—Cowan, Liebowitz & Latman P.C.; Mark Montague

(57) ABSTRACT

A method of obtaining an mRNA sequence having alternative spliced variants from a database of ESTs, comprising:
  providing a raw database comprising a plurality of ESTs; and
  assembling ones of said ESTs into mRNA sequences, wherein said assembling includes identifying alternative spliced regions.

14 Claims, 4 Drawing Sheets

METHOD AND APPARATUS FOR MRNA ASSEMBLY

FIELD OF THE INVENTION

The present invention relates to automatic assembly of mRNA sequences from databases containing large numbers of partial cDNA sequences.

BACKGROUND OF THE INVENTION

In human cells, genetic material is stored as DNA in a nucleus of the cell. When a certain protein is needed by the cell, a portion of the DNA is transcribed as mRNA, which is transported the cytoplasm of the cell. In the cytoplasm, ribosomes create proteins, using the mRNA as a template. Generally, the mRNA comprises a long sequence of bases, each triplet (codon) of which encodes a specific amino acid. Thus, a sequence of triplets encodes a sequence of amino acids, which form a protein.

Cell function can, theoretically, be analyzed by determining the type of and ratio between the proteins in the cell. However, proteins are very delicate materials, which are difficult to analyze. mRNA, which controls the creation of the proteins, is easier to separate and analyze. Although several different mRNA sequences may encode similar acting proteins, each mRNA sequence encodes only a single protein. In addition, there is usually a good correlation between the relative amount of different types of mRNA and the relative amounts of protein. It is thus possible to analyze cell function by analyzing the mRNA in a cell.

It should be noted that mRNA contains two types of information which are not evident from DNA. First, the relative concentration of the mRNA indicates the abundance of a particular protein. Second, in the process of transcribing DNA, changes, especially deletions, are made to the nucleotide sequence.

Differential analysis is used to generate standardized databases of human cellular activity by determining differences between gene expression in sick cells and healthy cells and between cells from different tissues. The result of a differential analysis between two cells is the difference in the type and expression level of mRNA sequences. In some cells, for example cancer cells, there is a higher concentration of certain proteins than in healthy cells of the same tissue. Determining these differences can help researchers determine how a cancer cell functions differently from healthy cells. Analysis of mRNA is currently being used to generate drug leads. For example, by selectively blocking these proteins which are more common in cancer cells, using designer-pharmaceuticals, it may be possible to disrupt the functioning of cancer cells, without significantly affecting the functionality of regular cells. Also when developing pharmaceuticals for bacterial, prion and viral infections, it is useful to design a pharmaceutical which selectively blocks proteins which are necessary for the life and/or reproduction of the disease agent, but which does not block proteins necessary for human cell survival.

Thus, it can easily be appreciated why pharmaceutical companies, research institutes and biotechnology companies maintain large databases of partial mRNA sequences. Such sequences, known as ESTs (Expressed Sequence Tag), often have associated information, such as the tissue type and/or disease type where the EST is expressed and/or the expression level of the EST in these situations. Some databases include complete mRNA sequences. In some cases, a genomic database can be analyzed to yield mRNA sequences, if the introns are correctly identified.

ESTs are generated using the following (greatly simplified) process: a cell is selected and disrupted; proteins and other cell structures are selectively disintegrated; mRNA sequences are isolated and converted to cDNA sequences; cDNA sequences are inserted into host cells, which can be cultured; individual host cells are disrupted; and a segment of DNA which includes the cDNA or original mRNA sequence at a known location thereof is located and read out.

Unfortunately, the art of reading mRNA sequences is not yet completely developed. The error rate of the reading increases with increasing length of the mRNA sequence. The common errors are insertion or deletion of bases, and errors in the identification of individual bases. At a certain sequence length, the error rate increases to a point where further reading is not possible. As a result, most ESTs are only 200–600 bases long, while an average mRNA sequence is typically 1000–3000 bases long.

In addition, EST databases contain many other types of errors, which may be accumulated during the complicated process of EST generation in addition to features, inherent in the mRNA, which make the assembly difficult. These causes of difficulty include:

(a) Chimeric sequences. During the process of extracting and replicating the mRNA and cDNA, chimeric sequences may be inadvertently inserted into the nucleotide sequences. Such chimeric sequences include ribosome RNA, junk sequences from the extraction and replication process, contamination from external sources, such as human cells and contamination from the host cells.

(b) Intron Contamination. Introns are portions of the DNA which are not expressed in the final mRNA product and are usually removed from the mRNA during the middle of the transcription process (splicing). However, since the cell is disrupted in the middle of its normal activity, the transcription process may be incomplete or otherwise disrupted, for example by introns being incorporated in the mRNA sequences.

(c) Broken and respliced sections. During the process of extraction and replication the mRNA sequences may be broken and, in some cases, may be reconnected, not necessarily correctly. In addition, whole sections of mRNA sequences may be inadvertently removed.

(d) Alternative splicing. This is not an error in the ESTs but it is an important cause of mismatch between ESTs. The transcription of DNA to mRNA does not follow a one-to-one correspondence. Depending on various conditions in the cell, a single DNA sequence may be transcribed as several different mRNA sequences. The different transcriptions, named alternative splice variants, are usually achieved by certain segments of the DNA being selectively spliced out. Thereafter, selected portions of the mRNA, named alternative spliced regions, are selectively spliced out of the mRNA sequence. As result, there may be two mRNA sequences which do not exactly match, even though they originate from the same DNA sequence and contain no errors.

(e) Redundancy Level. The process of extracting the ESTs includes replication of mRNA sequences and there is usually more than one copy of each mRNA in a living cell. In addition, as most databases contain ESTs extracted in many experiments, many ESTs can be expected to appear in several experiments. As a result, there is a high redundancy of ESTs in the raw database. However, due to the errors in reading out the ESTs, the ESTs will not exactly match. Also, even though there may be significant overlap between two or more ESTs, they will usually have different start and end points and different lengths. This lack of consistency makes the task of assembly more difficult.

As an end result, EST databases generally contain only short ESTs, which must then be correctly associated and assembled into the original mRNA sequences. However, due to the above-described problems, it is very difficult to correctly match up the ESTs. In general, the limiting factor in this field is information analysis, rather than information volume.

If the ESTs are correctly matched, the discovery and/or development of new pharmaceuticals, is made easier and faster. For example, assuming 20 ESTs are determined by differential analysis to be found in a cancer cell rather than a healthy cell, 20 leads must be pursued to find a drug, which may disrupt the cancer cell. However, if the 20 ESTs are combined to form 2 complete mRNA sequences, only 2 leads need to be pursued, reducing the volume of work by a factor of 10.

SUMMARY OF THE INVENTION

It is an object of some embodiments of the present invention to provide a method of mRNA assembly which reduces existing raw EST databases, removes errors therefrom and facilitates the creation of longer and/or complete mRNA sequences. The desired end result is a reduced database in which each mRNA sequence and/or EST encodes a different protein. At least, the ratio between the number of ESTs and the number of proteins should be reduced as much as possible. Two types of errors should preferably be avoided and/or corrected: incorrect mRNA sequences and errors of omission, where a real difference between two mRNA sequences is lost, due to the method of reducing the raw database.

It is another object of some embodiments of the present invention to provide a method of discovering hereunto unknown complete mRNA sequence and/or genes.

It is another object of some embodiments of the present invention to provide a method of modeling and discovering alternatively spliced mRNA sequences.

It is another object of some embodiments of the present invention to provide a method of EST association and/or assembly which has a lower computational complexity than existing methods and is therefore suitable for the analysis of huge databases of ESTs.

In accordance with a preferred embodiment of the present invention, a process of database reduction and/or analysis includes:

(a) correcting obvious errors in ESTs;

(b) clustering ESTs which appear to originate from the same mRNA sequence;

(c) assembling ESTs into mRNA sequences;

(d) comparing the assembled mRNA sequences to protein databases; and (e) comparing the assembled mRNA sequences to genome databases.

The order of (a)–(e) is not fixed. For example, error correction may be performed at any stage. Further, the process is preferably iterative, with later steps affecting earlier steps.

One aspect of some embodiments of the present invention relates to using a method that directly compares a database with a database, rather than a method that compares an individual EST with a database. As a result, a more efficient analysis algorithm can be developed. In accordance with a preferred embodiment of the invention, an algorithm whose complexity is near $O(k(N)xN)$, where k is a slowly increasing function of N, rather than $O(N^2)$, (N is the number of ESTs) is provided. In huge EST databases, this difference is extremely important and may pave the way to using mRNA analysis of cells from biopsies to diagnose individuals, in a short time.

Another aspect of some embodiment of the present invention, relates to a method of clustering ESTs. Rather than force a long segment of one EST to match a second segment of a second EST, only certain annotated portions of the ESTs are matched. In a preferred embodiment of the invention, short segments, preferably 9 bases long, are used for the matching. An index is generated which lists, for each 9 base sequence (n-group), all the ESTs which contain that sequence. The list associated with each indexing n-group may then be treated as an individual (smaller) database. If the component database is small enough, it may be preferred to use brute force methods to find matches within the component database. Alternatively or additionally, at least larger ones of the component databases may be reindexed using the same method. Preferably, during such reindexing additional limitations are applied, for example, that the order of appearance of the n-groups is the same in the matched ESTs or by indexing (and matching) only the n-groups which are either consecutive, 1 or 2 bases away from the indexing n-group. Typically, ESTs are clustered when they contain 4 matching n-groups.

It should be appreciated that the size of the indexing base sequence may be a number other than 9, although 9 appears to be suitable for raw databases of 100,000–1,000,000 ESTs of an average length of 400 bases. The length of the n-group may also be different for different iterations of the method. It should be appreciated that, in general, longer indexing sequences are more sensitive to errors in the reading of the mRNA sequences, however, they provide better matches. Further, the number of n-groups that must match is also a parameter, which may vary depending on the original database size, error rate and redundancy level. Further, the number of bases allowed between two consecutive n-groups is also a parameter, which may vary responsive to the database characteristics and the efficiency of the algorithm. In a preferred embodiment of the invention, each EST is graded as to its suitability to be included in a certain cluster. In some cases, an EST may be suitable for two clusters, especially if the two clusters are really a single cluster. In addition, externally provided data, such as the information that two ESTs are probably from the same mRNA sequence, can also affect the grade. Also the number of detected and/or corrected errors in a particular EST and/or in the original database as a whole may affect the grading process.

Another aspect of some embodiments of the present invention relates to a method of assembly of clustered ESTs into mRNA sequences using graphs. Each unique segment of an EST is associated with a node in a directed graph. The allowed transitions between nodes are restricted based on the "transitions" found in the ESTs that comprise the cluster. In accordance with a preferred embodiment of the invention, the resulting graph is analyzed to determine errors. For example, if there is more than one end node in the graph, this may be indicative of a chimeric sequence. Also an end node which is too close (number of bases between) to a start node is also usually indicative of a problem. End nodes may be defined as nodes whose segments contain stop codons and/or as nodes which have no transitions thereafter. Alternative paths in the graph, in which both a direct transition and an indirect transition between two nodes are available, usually identify alternative spliced regions. In a preferred embodiment of the invention, mRNA sequences with one, two, three, four or even more alternative spliced regions are correctly identified by preferred embodiments of the invention. Thus, a large number of possible alternative spliced variants, for a single mRNA sequence, may be identified in a single tissue type. Generally, the larger the ratio between ESTs and mRNA sequences, the better the identification of alternative spliced regions (and of errors in the sequence). Further, some preferred embodiments of the invention can also identify exclusive alternative splices, where each alternative spliced variant of the mRNA sequence contains a segment that does not appear in other variants.

Another aspect of some embodiments of the present invention relates to using feedback from one step of the above-described process to affect a different step. In one example, an error in the assembly step, such as the discovery of a chimeric sequence, may be used to change the clustering, by disallowing all matches based on the identified chimeric sequence. A chimeric sequence may be identified by matching the assembled mRNA sequence to a database of known contaminates. Preferably, only suspected chimeric sequences are tested by comparison to a database of contaminates, at the assembly stage. Suspicious sequences are preferably determined from the morphology of the graph. Another example is correcting errors in ESTs based on the assembly. Such corrected errors may also be propagated back to the clustering step.

Another aspect of the present invention relates to using an mRNA assembly method as a part of a diagnostic device. Such a device will receive as an input a readout of ESTs, sequence the ESTs into mRNA sequences, correct errors in the sequences and then analyze the resulting mRNA expression spectra and/or compare it to known disease templates to diagnose the disease. Such an input may, in some cases be of relatively low quality.

Another aspect of some embodiments of the present invention is related to diagnosing diseases and cellular dysfunction based on an analysis of relative expression levels of alternative spliced variants in a single tissue type.

Another aspect of the present invention relates to DNA chip design. Correct selection of DNA sequences to place on a DNA chip is limited by the uncertainty of the relative importance and association of different ESTs. Once the ESTs are assembled into mRNA sequences, it is possible to select one or more sets of DNA segments which will be most useful for the DNA matching task. The high degree of automation possible with—and the quality of—mRNA sequence determination, in accordance with preferred embodiments of the present invention, make such an analysis for DNA chip design a reality. Such a set can also take into account alternative splicing and/or the types and distributions of different errors in the EST database. Thus, a DNA chip can be made more robust for a particular application. In one preferred embodiment of the invention, the indexing method is used to generate an index of all the short segments of nucleotides in the mRNA sequences of interest. The length of the short segments is determined based on the design constraints of the DNA chip. The number of short segments necessary to correctly identify a single mRNA sequence (or DNA sequences, in genomic applications) can be determined by the number of re-indexing steps required to isolate that sequence in a database. The utilization of a DNA chip can be maximized by selecting only mRNA sequences which can be identified using a minimal number of short DNA sequences.

There is therefore provided in accordance with a preferred embodiment of the invention, a method of obtaining an mRNA sequence having alternative spliced variants from a database of ESTs, comprising:

providing a raw database comprising a plurality of ESTs; and assembling ones of said ESTs into mRNA sequences, wherein said assembling includes identifying alternative spliced regions.

Preferably, the method includes clustering ESTs which have matching segments and wherein said assembly comprising assembling ESTs which are clustered together.

Alternatively or additionally, the method includes correcting errors in said ESTs.

There is also provided in accordance with a preferred embodiment of the invention, an mRNA sequence determined by the above described processes. Preferably, the sequence comprises at least two alternative spliced regions. Alternatively, the sequence comprises at least three alternative spliced regions. Alternatively, the sequence comprises at least four alternative spliced regions. Alternatively or additionally, the sequence represents at least two alternative spliced variants of mRNA sequence, each variant utilizing at least one mutually exclusive alternative splice region. Alternatively, the sequence represents at least three alternative spliced variants of mRNA, each variant utilizing at least one mutually exclusive alternative splice region. Alternatively or additionally, the sequence represents at least four alternative spliced variants of mRNA, each variant utilizing at least one mutually exclusive alternative splice region. Alternatively, or additionally, the mRNA sequence is obtained from a single tissue type.

There is also provided in accordance with a preferred embodiment of the invention, a method of tissue analysis comprising:

providing a biological sample;

determining relative expression levels of different variants of mRNA sequences in the biological sample which contain alternative spliced regions, to determine a spectra of relative expression of alternative spliced variants; and analyzing said spectra to determine disease in the sample.

Preferably, analyzing comprises comparing said spectra against predetermined spectra. Alternatively or additionally, determining relative expression levels comprises:

analyzing said sample to detect ESTs; and assembling said ESTs into mRNA sequences having alternative spliced regions.

There is also provided in accordance with a preferred embodiment of the invention a diagnostic device comprising:

an input for receiving EST expression levels; and a spectra generator which generates a spectra of mRNA expression levels responsive to said EST input.

Preferably, the spectra generator generates a spectra of relative expression levels of different variants of mRNA sequences containing alternative spliced regions. Alternatively or additionally, the device comprises a database containing expression spectra corresponding to a plurality of disease states. Preferably, the device comprises a comparator which compares the generated spectra with spectra in the database to determine a disease state in the tissue which originated the ESTs.

There is also provided in accordance with a preferred embodiment of the invention, a method of clustering a plurality of ESTs, comprising:

indexing n-groups in the ESTs, to generate lists of ESTs which contain each particular n-group indexed; and matching ESTs within each list to generate clusters.

Preferably, matching ESTs comprises indexing n-groups in each of said lists to generate secondary lists. Preferably the method comprises recursively applying said indexing until recursively created secondary lists include ESTs containing at least three n-group matches. Alternatively, the method comprises recursively applying said indexing until recursively created secondary lists include ESTs containing at least four n-group matches. Alternatively the method comprises recursively applying said indexing until recursively created secondary lists include ESTs containing at least five n-group matches. Alternatively or additionally, recursively applying said indexing comprises recursively indexing only n-groups which are distanced from the first indexed n-group less than a certain number of bases. Preferably, the number of bases is less than five. Alternatively, the number of bases is less than four. Alternatively, the number of bases is less than three.

Alternatively or additionally, matching comprises correlating said ESTs using an SW (Smith-Waterman) algorithm, modified to include detection of long-gaps.

Alternatively, matching comprises correlating said ESTs using an SW (Smith-Waterman) algorithm.

In a preferred embodiment of the invention, said indexing comprises ignoring certain n-groups.

Preferably, the indexed n-groups are 9 bases long. Preferably, the n-groups are between 5 and 15 bases long.

In a preferred embodiment of the invention the clustering method includes merging clusters. Preferably, merging clusters comprises merging responsive to an assumed error distribution in said ESTs.

There is also provided in accordance with a preferred embodiment of the invention, a method of mRNA assembly from a plurality of ESTs, comprising:

determining a correspondence between segments in each EST; and generating a directed graph in which each node represents a single segment, and each transition between two nodes represents the existence of an EST in which the two corresponding segments are consecutive.

Preferably, the method comprises clustering said ESTs into clusters of associated ESTs, wherein said determining a correspondence is performed on individual clusters of ESTs. Alternatively or additionally, the method comprises identifying alternative spliced regions from said graph based on the morphology of the graph. Alternatively or additionally, the method comprises correcting errors in said ESTs based on said graph based on the morphology of the graph. Preferably, the method comprises repeating said clustering responsive to said corrected errors.

There is also provided in accordance with a preferred embodiment of the invention a method of identifying errors in mRNA sequences, comprising:

generating a graph which represents the assembly of segments of ESTs into an mRNA sequence; and analyzing said graph to determine unusual configurations of said graph.

Preferably, said analyzing comprises identifying multiple end-nodes in said graph.

There is also provided in accordance with a preferred embodiment of the invention a method of tuning a database reduction process, comprising:

applying the database reduction process, with a certain value for at least one parameter, to a sample database;

determining a reduction ratio in the database; and reapplying said method with a new value for said at least one parameter if said reduction ratio is not achieved.

Preferably, the at least one parameter comprises the length of n-groups used in matching two ESTs.

There is also provided in accordance with a preferred embodiment of the invention a method of iterative clustering of ESTs, comprising:

clustering ESTs;

assembling clustered ESTs; and re-clustering the ESTs responsive to errors detected in the ESTs after said clustering.

There is also provided in accordance with a preferred embodiment of the invention, a method of iterative clustering of ESTs, comprising:

deciding if two ESTs match, responsive to predetermined error probabilities of errors in said ESTs;

clustering said ESTs responsive to said match;

correcting said predetermined error probabilities, responsive to further processing of said ESTs; and repeating said deciding and said clustering responsive to said corrected error probabilities.

There is also provided in accordance with a preferred embodiment of the invention a method of EST database processing, comprising:

analyzing said ESTs to detect errors;

further processing said ESTs to create mRNA sequences;

determining, responsive to said further processing, corrections for said errors; and correcting said errors.

Preferably, said further processing comprises assembling said ESTs into mRNA sequences.

There is also provided in accordance with a preferred embodiment of the invention, a method of designing a DNA chip based on an EST set determined by differential analysis of two biological samples, comprising:

reducing said EST set to a set of mRNA sequences;

analyzing said set of mRNA sequences to determine short mRNA sequences which maximally differentiate said mRNA sequences from mRNA sequences found in both biological samples; and designing a DNA chip which detects said short mRNA sequences.

There is also provided in accordance with a preferred embodiment of the invention, a method of designing a DNA chip to detect relative expression levels of different variants of mRNA sequences having alternative spliced regions, comprising:

reducing an EST database to determine an mRNA sequence having alternative spliced regions;

enumerating short DNA sequences which are only included in the alternative spliced regions of said different variants; and designing a DNA chip which detects said short DNA sequences.

There is further provided in accordance with a preferred embodiment of the invention a DNA chip constructed based on the above design methods.

There is also provided in accordance with a preferred embodiment of the invention, an mRNA sequence comprising at least two alternative spliced variants, for a single tissue type. Preferably, the sequence comprises at least three alternative variants. Preferably, the sequence comprises at least four alternative variants.

There is also provided in accordance with a preferred embodiment of the invention, an mRNA sequence comprising at least three alternative spliced regions. Preferably, the sequence comprises at least four alternative spliced regions. Preferably, the sequence comprises at least five alternative spliced regions. Alternatively or additionally, the mRNA sequence comprises different variants including mutually exclusive regions.

There is also provided in accordance with a preferred embodiment of the invention, a method of designing a DNA chip, comprising:

indexing an mRNA database to determine the indexing of short DNA sequences in the mRNA database, which short DNA sequences are of a length suitable for detection by a DNA chip;

determining from said indexing a set of short DNA sequences which uniquely identify a desired mRNA sequence; and designing a DNA chip which detects said set of short DNA sequences.

There is also provided in accordance with a preferred embodiment of the invention an mRNA sequence substantially as described and shown in mRNA transcripts included in the instant application.

There is also provided in accordance with a preferred embodiment of the invention an mRNA sequence having alternative spliced variants, substantially as described and shown in the instant application.

BRIEF DESCRIPTION OF THE DRAWINGS

The present invention will be more clearly understood from the detailed description of the preferred embodiments with reference to the accompanying figures, in which.

DETAIL DESCRIPTIONS OF PREFERRED EMBODIMENTS

Figure 1:
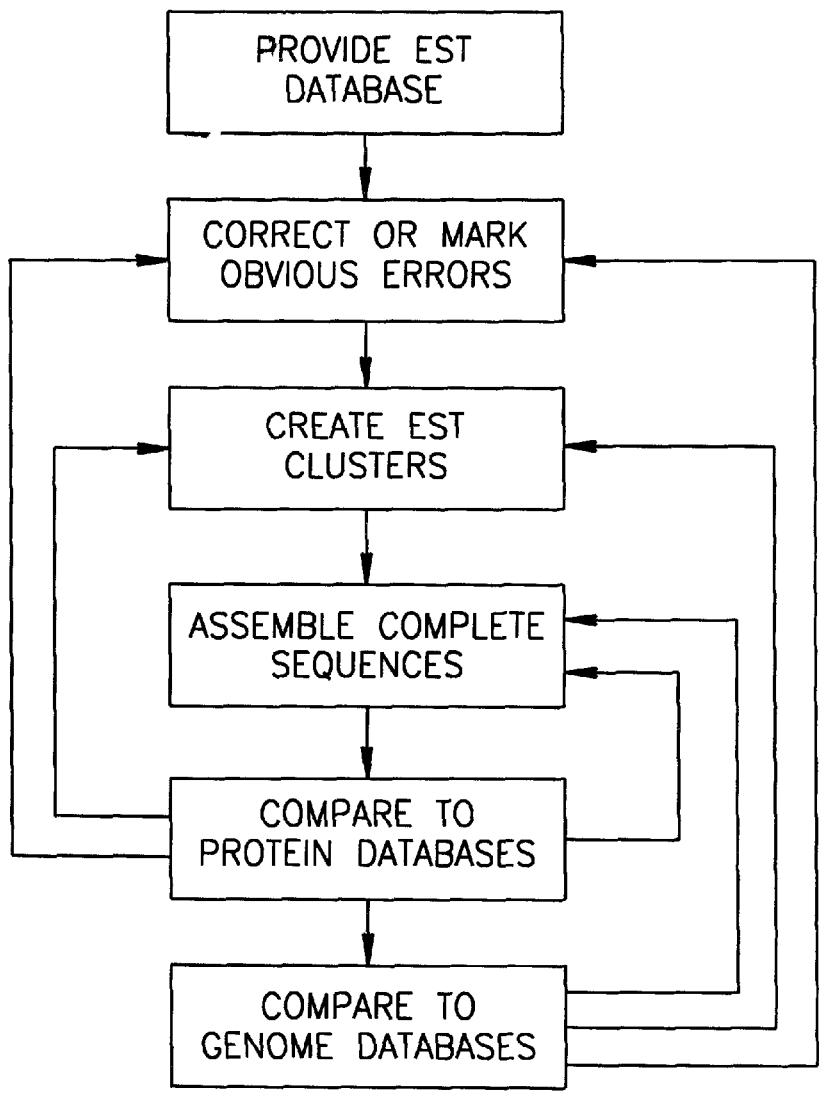
FIG. 1 is a flowchart of a method for generating mRNA sequences from a database of ESTs, in accordance with a preferred embodiment of the invention.

FIG. 1 is a flowchart of a method for generating mRNA sequences from a database of ESTs, in accordance with a preferred embodiment of the invention. The databases usually contain raw data and may be provided either from an existing EST database or by analyzing a particular cell to determine ESTs therefrom, possibly using a method well known in the art. Thus, the first step is preferably automatic correction of obvious errors. It should however be noted, the error correction may be performed at additional or alternative steps in the process.

ERROR IDENTIFICATION AND CORRECTION

It should be noted that some errors, which may seem obvious, may turn out, at a later stage, not to be errors at all. Thus, an important aspect of error correction is preferably error identification. Further, in some cases, errors will be identified at an earlier stage and corrected only at a later stage (when they are confirmed). In a preferred embodiment of the invention, any errors that are corrected are preferably marked, so that such corrections may be automatically undone, if needed.

There are two types of error identification schemes which are preferably used:

(a) Analysis of the original readout data (trace information) to provide the probability of correct identification of bases. This information may be stored in the database. In some cases the probabilities of error in bases identification is dependent on the equipment used to read the ESTs. In a preferred embodiment of the invention, error probabilities are assigned based on the type of equipment and/or other characteristics of the readout process. In another preferred embodiment of the invention, error probabilities are determined and/or updated by analyzing the type and distribution of errors in mRNA sequences which were identified in an earlier iteration of the process. In a preferred embodiment of the invention, such an earlier iteration is limited to assembling mRNA sequences which are known to be in the raw database. Thus, when the ESTs associated with the mRNA sequence are found, the distribution of different types of errors can be determined by comparing the ESTs with the known correct mRNA sequence. Such a limited iteration may use EST-to-database matching techniques, which are known in the art or it may use a subset of the techniques described herein.

(b) Analysis of the ESTs to detect suspicious portions, for example multiple repeats of single bases or short sequences.

There are several types of errors that are preferably corrected at this stage:

(a) Extra strings of "A" type bases. During the process of maturation of the mRNA, a long string of "A" bases are usually attached to the mRNA. Although these strings are generally automatically removed, some such strings may remain as contaminates and disrupt the assembly of mRNA sequences.

(b) Host DNA. The sequence of DNA just prior to and just after the mRNA, in the host cell, is well known, so a contamination by such a sequence can be easily detected and removed.

(c) Insertions and deletions. Missing and extra bases can usually be detected, since they render the rest of the mRNA sequence to be nonsense. mRNA, unlike DNA, does not usually contain nonsense segments and especially not series of stop codons. In some cases the missing base can also be guessed at or the range of possibilities narrowed, by presuming that the resulting codon must be for an amino acid. Alternatively, a blank codon is inserted and the correct codon is determined during the assembly step, described below. Further alternatively, no codon is inserted, but the error is preferably noted.

CLUSTERING

Figure 2:
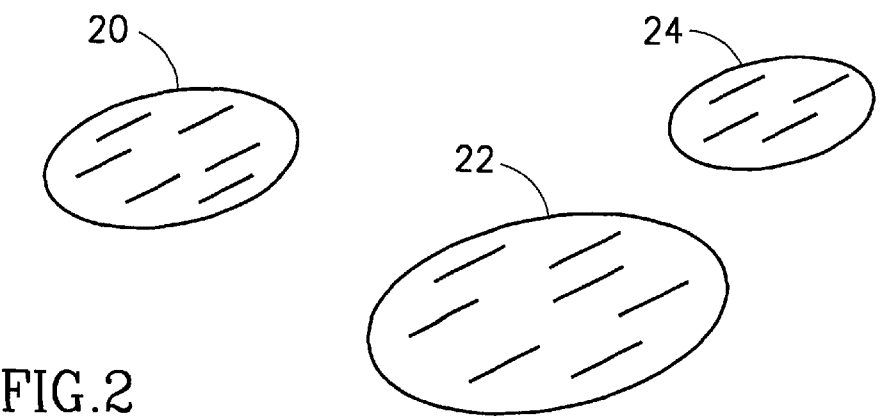
FIG. 2 is a schematic illustration of ESTs clustered into a number of exclusive clusters.

After the ESTs are corrected for obvious errors, they are clustered into groups, each group supposedly containing ESTs from only a single gene. FIG. 2 is a schematic illustration of ESTs (indicated as short lines) clustered into three clusters 20, 22 and 24. In a typical raw database, containing over a million ESTs, the number of expected clusters is about 20,000–50,000.

Figure 3:
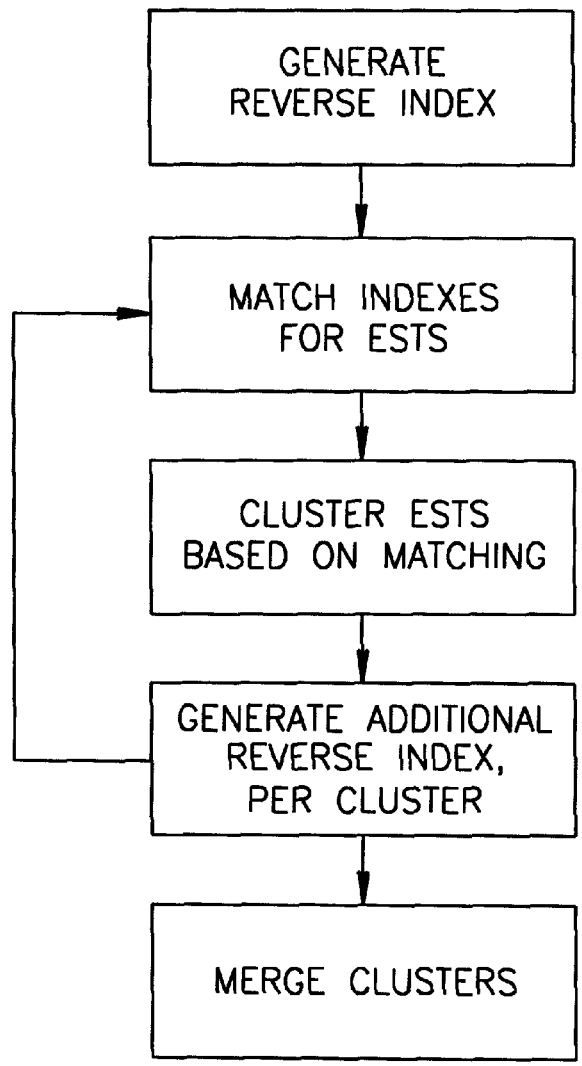
FIG. 3 is a flowchart of a method for EST clustering, in accordance with a preferred embodiment of the invention.

FIG. 3 is a flowchart of a method for EST clustering, in accordance with a preferred embodiment of the invention. Rather than attempt to analyze the entire database in one go, the database is divided into component databases (some of which will usually overlap). Each such component database is preferably generated by indexing the entire database, described in more detail below. Matching ESTs is then performed in each of these component databases. At a later stage, the analyzed component databases, significantly reduced in size, may be merged together. The computational complexity of the matching task with the merged database is thus substantially reduced over that with the whole original database. It should be noted that the division into component databases is preferably strongly related to the EST matching. So dividing up the database does not adversely affect the completeness of EST matching in the database as a whole.

Figure 4:
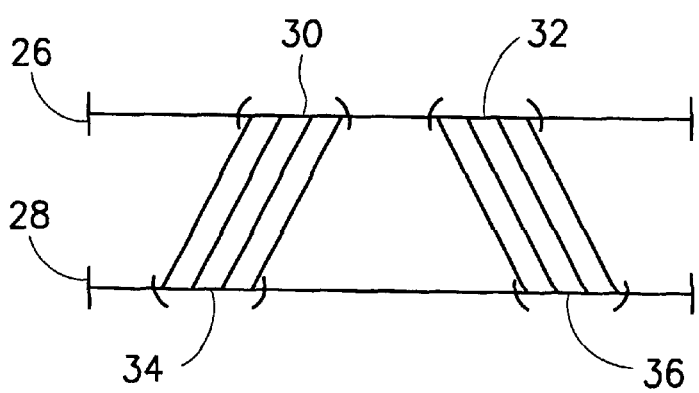
FIG. 4 is a schematic illustration of a partial matching between two ESTs, in accordance with a preferred embodiment of the invention.

FIG. 4 is a schematic illustration of a partial matching between two ESTs 26 and 28. A segment 30 in EST 26 matches a segment 34 in EST 28 and a segment 32 in EST 26 matches a segment 36 in EST 28. Instead of trying to match long segments of EST 26 and EST 28, in accordance with a preferred embodiment of the invention, only short segments are matched. It should be appreciated that the error rate in EST sequences is several percent, thus, the longer the segment matched, the higher the chance of missing a proper match, due to errors in the ESTs. However, when shorter segments are used, the number of matches between unrelated ESTs increase. One aspect of some embodiments of the present invention solve this problem by iteratively applying a matching process. Preferably, the number of bases in the segment matched is 9 (an n-group). However, this number is preferably a parameter dependent, inter alia, on the database size. A group of 9 bases is typically suitable for a database of several hundreds of thousands of ESTs, each EST of between 200 and 600 bases long. In other sizes of databases, other values may be used, preferably in the range 5–20, more preferably in the range 7–11.

Figure 5:
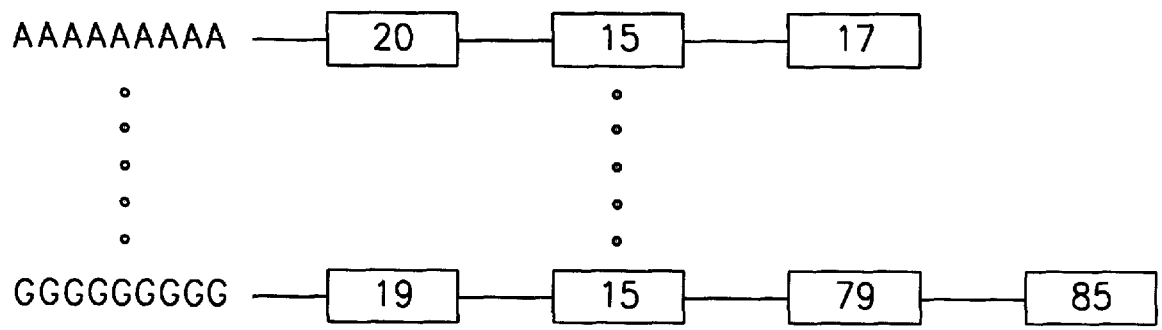
FIG. 5 is a schematic illustration of an index of an EST database, by n-groups, in accordance with a preferred embodiment of the invention.

In a preferred embodiment of the invention, the first step of clustering comprises generating an index of all the n-groups in the EST database. FIG. 5 is a schematic illustration of an index of an EST database, by n-groups, in accordance with a preferred embodiment of the invention. Each n-group has associated therewith a list of all the ESTs that contain that n-group anywhere in the EST (not only on boundaries of triplets). Each of these lists defines a database, within which all the ESTs may be related. There is, of course, the possibility of two related ESTs not being in the same list. Also, two ESTs might have a matching n-group even if they are completely unrelated. In addition, the same EST will probably appear in a very large number of lists, generally a monotonic increasing function of the length of the EST. The location of the n-group in the EST is also associated with each element of the list. If an n-group appears more than once in an EST, it is preferably entered in the list several times, each time with a different associated location of the n-group.

Each of the lists of a common n-group can, as described above, be treated as an individual database, with any type of EST matching method known in the art performed thereon. However, in a preferred embodiment of the invention, especially when the list is very long, the above-described method of indexing is reapplied. The resulting second-order lists contain ESTs in which two n-groups match. Preferably, the process is repeated until there are four matching n-groups in each list. In a preferred embodiment of the invention, the reindexing is performed by intersection between the list of the common n-group and lists corresponding to other n-groups. The resulting lists may be used as seed clusters. The number of matching n-groups is also a parameter which may depend on, inter alia, on database size and error distributions.

In a preferred embodiment of the invention, at least some of the re-applications of the indexing method, include adding additional limitations. One type of limitation is requiring that the order of the matched n-groups be the same in matched ESTs. Another type of limitation is that at least some of the n-groups must be distanced by a minimum number of bases from other n-groups, thus a larger overlapping segment between ESTs is required for them to match. Yet another type of limitation is that the matched ESTs be substantially consecutive.

In this last type of limitation, rather the re-index all the n-groups in the ESTs, only the n-groups which are consecutive with, or distanced by a small number of bases, such as 1 or 2, from the common n-group, are indexed. Of course, other distances between the n-groups, such as distances smaller than 20 and more preferably, smaller than 10, may also be used. By requiring such a short distance between consecutive matching n-groups, an effective 18-group is formed and a match between two ESTs implies a match of 18 consecutive bases (27 and 36 in later iterations). However, by allowing 0, 1 or 2 bases to appear between the n-groups, small insertions and deletions of bases may be overcome. In addition, using such short matching sequences allows even rather short ESTs, such as EST fragments, to partake in the clustering process.

It should be appreciated that some of the index lists are longer than others. In some animal species, the occurrence of some n-groups is more common than in others. In addition, due to statistical considerations, some n-groups will be more common than others. It should be noted that if an n-group is too common, the number of correct associations between ESTs using that n-group will be significantly lower than the number of incorrect ones. This is especially true for poly-A sequences and for repetitive DNA sequences. In a preferred embodiment of the invention, clustering is started from the shorter lists, i.e., those which correspond to the less common sequences. Preferably, once all, or most, of the ESTs are clustered, the clustering is stopped. Alternatively or additionally, lists containing more than a certain percentage of ESTs are ignored. Thus, not all the component databases need to be processed. This percentage is preferably a parameter, preferably dependent on the database size and of the type of distribution of the n-groups. In a preferred embodiment of the invention, a database of n-groups less preferred for matching is maintained and, if possible, lists corresponding to these n-groups are not indexed and/or ignored. Alternatively or additionally, the more common n-groups are not indexed at all. In a preferred embodiment of the invention, the relative distribution of n-groups is determined by indexing a statistically significant sample of the EST database.

In a preferred embodiment of the invention, n-groups of portions of ESTs, which include errors, and/or n-groups of portions of ESTs, which include corrected errors, do not participate in the indexing. Preferably, once the errors are corrected, these n-groups are indexed and the clustering is updated. Alternatively, such n-groups are graded with a lower grade than (supposedly) error-free n-groups. The decision whether to associate an EST with a cluster may be made based on the grade. Further, even if no errors are detected, some n-groups may be assigned a lower grade than other n-groups, for example n-groups of consecutive bases of a single type. Still further, a particular EST may be assigned a lower grade than other ESTs due to problems which occur during the reading of the EST. Matching this EST to a cluster will preferably require a higher definiteness of matching, such as requiring five matching n-groups instead of four.

Once the ESTs are grouped into seed clusters, the clusters are preferably merged into large clusters. In a preferred embodiment of the invention, a Union-Find algorithm, which is known to have a low computational complexity, is used to perform the merge. Since a same EST can appear in more than one seed cluster, any two clusters which include the same EST may be merged. In addition, sometimes two ESTs are known to be from the same mRNA sequence, for example, when they are read out from opposite sides of the same mRNA. In this case, clusters containing these ESTs may also be merged. In some cases, two clusters will not be merged, based on feedback from a later stage in the processing. One example of such feedback is the identification of a common EST or of a matched portion of an EST as a chimeric segment. In a preferred embodiment of the invention, an existing cluster may be split apart and the assembly thereof repeated. In this embodiment, the history of the matches, which merged the cluster, are preferably saved, to facilitate splitting it. Alternatively, the cluster may be split by identifying the incorrect matches and then splitting the cluster based on the remaining matches.

In a preferred embodiment of the invention, the correspondence between the ESTs is used as a starting point for the assembly step, described next.

ASSEMBLY

Figure 6:
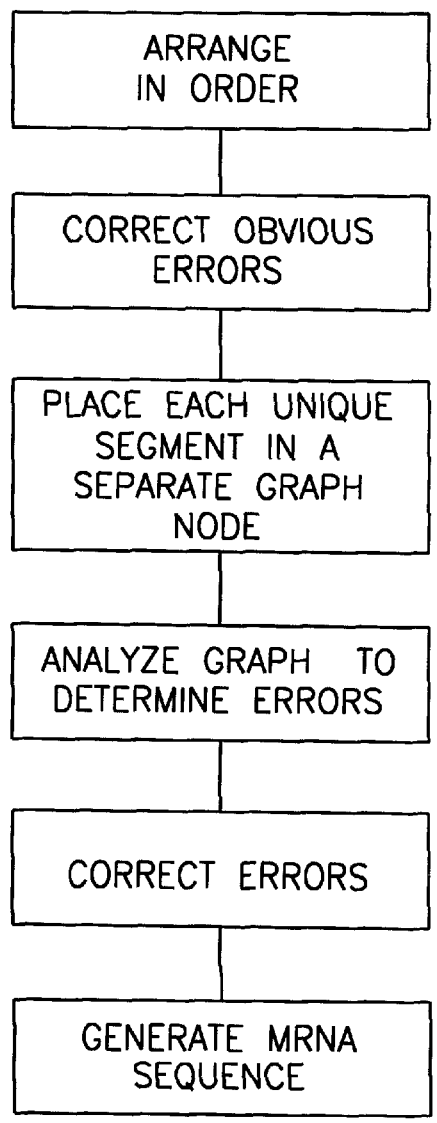
FIG. 6 is a flowchart of a method of assembling clustered ESTs, in accordance with a preferred embodiment of the invention.

FIG. 6 is a flowchart of a method of assembling clustered ESTs, in accordance with a preferred embodiment of the invention. First, the ESTs are arranged with corresponding segments of the ESTs identified. In the clustering step of the algorithm, two ESTs were associated if they had four consecutive corresponding n-groups. When the ESTs are arranged for assembly, it is expected that the corresponding segments be substantially longer.

In accordance with one preferred embodiment of the invention, the segments are identified and matched using a standard algorithm such as a correlation algorithm, a BLAST algorithm, a FASTA algorithm or an SW (Smith-Waterman) algorithm. Alternatively, the matching of ESTs is performed by expanding the matching of the n-groups to adjacent bases, until each segment of each EST, is either matched to a corresponding segment or determined to be unmatched. Typically, there will be some vagueness regarding the exact extent of the segments, especially at the ends of ESTs. This may be due to missing bases at the ends of the ESTs. In addition, there is not usually an exact match between two segments due to errors in the ESTs. These types of errors are preferably corrected as described below.

In a preferred embodiment of the invention, an identified segment is split (and the split propagated to other ESTs where the segment has been identified) when the segment matches only a part of a corresponding segment in a different EST. Preferably, the correlation level at which a segment is split is a parameter of the system.

One problem with best match correlations between two ESTs is that similar ESTs can originate from different, yet homologous genes. In a preferred embodiment of the invention, two segment matching algorithms are used to align the ESTs, one algorithm which attempts to detect that two ESTs are from homologous genes and one which attempts to detect that the ESTs are from the same gene. Alternatively, a single algorithm is used, which generates a probability of two ESTs being from the same gene, from homologous genes or unrelated. One example of algorithms which attempt to detect that two ESTs are from homologous genes is the GeneWise family of algorithms. The previously described correlation, BLAST, FASTA and SW algorithms attempt to detect that two ESTs are from the same gene.

In a preferred embodiment of the invention, a modified SW type algorithm is used to generate correspondences between ESTs. In a regular SW algorithms, a penalty is attached for each missing or extra base. In accordance with a preferred embodiment of the invention, the following grading scheme is used, which includes a new situation, "long gap":

First Gap: 12 penalty points

Following Gaps: 4 penalty points

Match: 4 bonus points

Mismatch: 9 penalty points

Long Gap: 50 penalty points

Thus, long gaps, which correspond to alternative spliced regions extract a large penalty, however, they do not generate as many penalty points as under the unmodified SW algorithm.

In one preferred embodiment of the invention, generating the correspondence between EST pairs is performed as part of the clustering.

Figure 7:
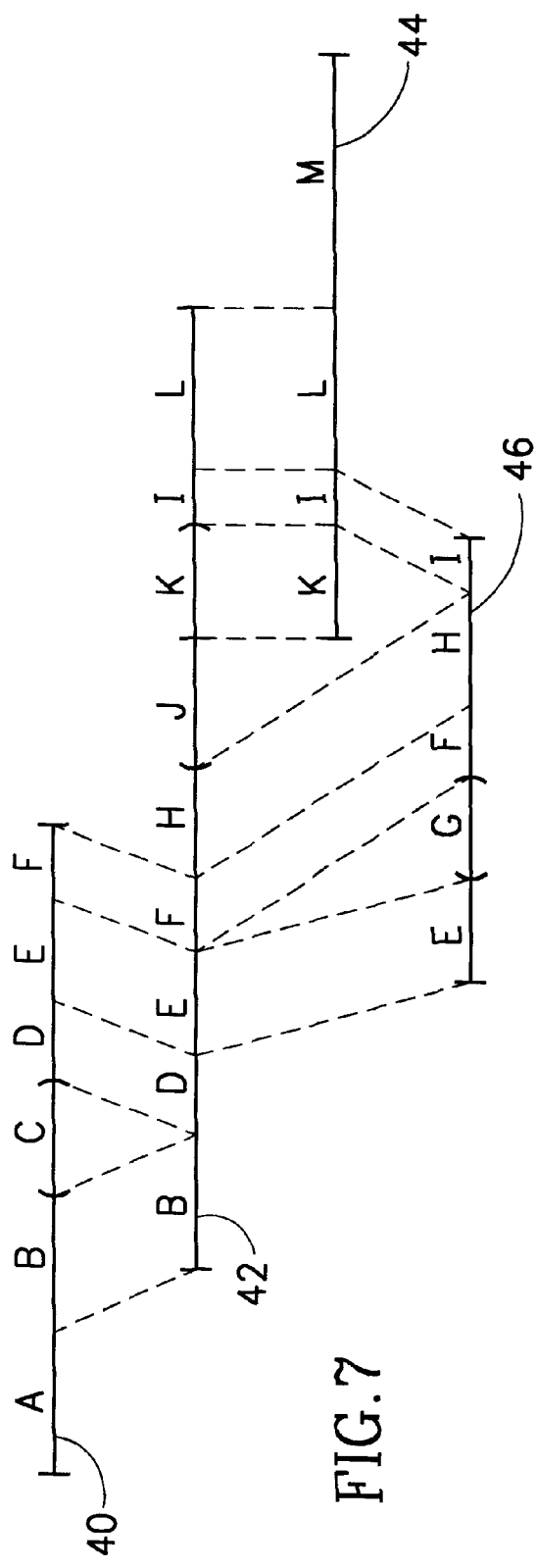
FIG. 7 is a schematic illustration of matched ESTs.

FIG. 7 is a simplified schematic illustration of four ESTs 40, 42, 44 and 46 arranged to show correspondence between segments thereof. In a typical database, there will be many more than four ESTs for each mRNA sequence. Before actually assembling an mRNA sequence, the overlap between the segments of ESTs is preferably used to correct errors in the ESTs. The corrections performed preferably include:

(a) replacing single bases with other type bases, preferably based on a voting algorithm between all the corresponding segments; and (b) correction of insertions or deletions of single bases, or a small number thereof, preferably based on a voting algorithm.

Once the corresponding segments are corrected, a directed graph is built to represent the cluster. In this graph, each node represents a single segment and the allowed transitions between nodes are exactly those transitions which correspond to two segments being consecutive. Alternatively, some or all of these corrections are performed only after the graph is generated and/or analyzed to correct errors. In a preferred embodiment of the invention, two nodes in which the origin node has only one exit and the ending node has only one input are collapsed into a single node, to simplify the resulting graph. In a normal situation, with no alternative splices, a single node, which represents the consensus of ESTs may suffice for describing an mRNA sequence. In a preferred embodiment of the invention, the graph is built incrementally by adding the effects of ESTs to the graph, on a one by one basis. A new EST will generally modify an existing graph by adding a new segment or by bridging two existing (possibly unconnected) segments. For example, two ESTs might be known to be associated because they are from opposite ends of a single mRNA sequence. However, until the gap between the sequences is bridged by one or more EST, it is not possible to determine their exact correspondence. Preferably, the graph is stored with the reduced database to facilitate adding further ESTs to the graph and/or database later.

Figure 8:
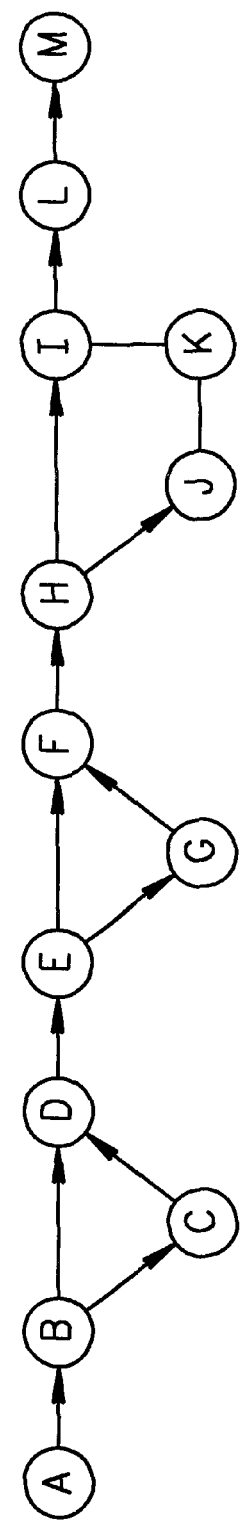
FIG. 8 is a illustration of a graph corresponding to the ESTs of FIG. 7, in accordance with a preferred embodiment of the invention.

FIG. 8 is a illustration of a graph corresponding to an assembly of ESTs 40, 42, 44 and 46 of FIG. 7, in accordance with a preferred embodiment of the invention.

An exemplary process of building the graph of FIG. 8 is as follows:

(1) a graph having a single node A is generated, where node A corresponds to segment A of EST 40;

(2) a new node B is generated for segment B which is common to ESTs 40 and 42;

(3) a transition between node A and node B is defined, based on their being consecutive in EST 40;

(4) a new node C is generated for segment C of EST 40;

(5) a transition between node B and node C is defined, based on their being consecutive in EST 40;

(6) a new node D is generated for segment D which is common to ESTs 40 and 42;

(7) a transition between nodes C and D is defined, based on their being consecutive in EST 40;

(8) a transition between nodes B and D is defined, based on their being consecutive in EST 42;

(9) a new node E is generated for segment E which is common to ESTs 40, 42 and 46;

(10) a transition between nodes D and E is generated, based on their being consecutive in EST 40 and EST 42;

(11) a new node F is generated for segment F which is common in ESTs 40, 42 and 46;

(12) a transition between nodes E and F is generated, based on their being consecutive in EST 40 and EST 42;

(13) a new node G is generated for segment G of EST 46;

(14) a transition between nodes E and G is defined based on EST 46;

(15) a transition between nodes G and F is defined based on EST 46;

(16) a new node H is generated for segment H which is common to ESTs 42 and 46;

(17) a transition between nodes F and H is defined based on EST 42 and EST 46;

(18) a new node I is generated for segment I in EST 46;

(19) a transition between nodes H and I is defined based on EST 46;

(20) a new node J is generated for segment J which is found only in EST 42;

(21) a transition between nodes H and J is defined based on EST 42;

(22) a new node K is generated for segment K in ESTs 42 and 44;

(23) a transition between nodes J and K is defined based on EST 42;

(24) a transition between nodes K and I is defined based on ESTs 42 and 44;

(25) a new node L is generated for segment L in ESTs 42 and 44;

(26) a transition between nodes I and L is defined based on ESTs 42 and 44;

(27) a new node M is generated for segment M in EST 42; and

(28) a transition between nodes L and M is defined based on EST 44.

As previously mentioned, some of the nodes may represent very short segments. The minimum length of segment is preferably a parameter. In a preferred embodiment of the invention, such short segments are either ignored (dropped, as a type of error correction) and/or attached to an adjacent node. One example in FIG. 8 would be if segment J was such a short segment. In addition, the final mRNA sequence preferably includes the end UTRs.

In a preferred embodiment of the invention, each node stores the original segments of the ESTs, their correspondence and/or any error correction performed thereon. Preferably, each node also stores a representation of the mRNA sequence which is created by merging these segments. Thus, when matching an EST to a node, the EST can be matched to any of the original ESTs and to the error corrected result of their combination.

The graph in FIG. 8 indicates that the mRNA sequence contains three alternative spliced regions: C, G and JK. However, it should be appreciated that from the information contained in the ESTs, there is no clear indication whether each of these alternative spliced regions is independent from each other. In a preferred embodiment of the invention the graph includes information which limits transitions based on previously selected transitions, responsive to dependencies between alternative spliced variants found in the EST database. In a preferred embodiment of the invention, either a "closed world assumption" or an "open world assumption" is used to decide whether a certain transition is allowed, based on the types of transitions found in the ESTs.

In accordance with a preferred embodiment of the invention, the resulting graph is analyzed to detect errors in the reading out of the mRNA. As described above, alternative spliced regions are clearly indicated by cycles in the graph. In some cases, where the alternative spliced region is at the end of the graph, the graph may have two ending points. An ending point may also have transition to other nodes (for example node L in the example of FIG. 8) if a very large number of ESTs end at segment L (even without a stop codon) and only a small number continue. Such a case may also indicate that segment M is an artifact or a rare alternative splice. The length of segment M and the number and the average overlap between ESTs may be used to determine whether segment M is an artifact. Preferably, such determination is based on statistics gleaned from other mRNA sequences in the database or in similar databases.

Chimeric sequences usually create artifacts in the graph. For example, if the resulting graph comprises a first start node and a first end node connected by a single transition and a second start node and a second end node also connected by a single transition, this graph corresponds to two mRNA sequences. However, if there is an extra transition between the first start node and the second end node, this transition may be indicative of a chimeric sequence. This suspicion becomes a near certainty if this transition is supported by only a single EST.

In accordance with a preferred embodiment of the invention, the following algorithm is used to generate a graph from ESTs. This algorithm assumes that an existing graph already exists and that a new EST is to be added to the graph. The first EST will generate a graph having a single node, which node will include a segment corresponding to the entire EST. It should be noted that this algorithm does not require that all the nodes of the graph be connected. The algorithm is:

(a) Match the new EST to the segments stored in each node of the graph.

(b) If the EST matches a node or a sequence represented by a contiguous series of nodes, the EST is merged with the nodes that it corresponds to.

(c) If a portion of the EST does not match, a new node is created for that portion. If the new node is at one of the ends of the graph, it may be incorporated in an existing node and used to extend the length of the segment represented by the node.

(d) If there is an extra or missing portion in the EST, which corresponds to the middle of a segment in an existing node, the existing node is split, a new node is generated for the none-matching portion and transitions are created between the two parts of the original node and between the new node and those parts of the existing node which match portions of the EST.

(e) A new transition is created between two existing nodes if the EST contains a contiguous sequence, the ends of which match portions of the two existing nodes.

In a preferred embodiment of the invention, a grammar is used to describe the gene sequences, where each token corresponds to a base or a segment, instead of or in addition to a graph type representation. For example, an LR(1) grammar or an LALR(1) grammar, may be used. In such a case, the errors in the gene sequences are preferably determined by applying grammar matching rules to the gene sequences. Preferably, each grammar matching rule is associated with a probability of a particular type of error. One example is using LEX, YACC or other lexical and/or grammar programs, known in the art.

It should be noted that, by using the graph type representation, more than one configuration of mRNA sequence, each of which corresponds to a different alternative spliced variant of a single mRNA sequence, can be detected in a single tissue type. Further, other types of mRNA variants, such as those caused by mutated genes and/or by other causes can also be detected. In addition, the ratio between two (or more) alternative spliced variants is preferably determined by counting the number of ESTs associated with each mRNA configuration and/or by comparing their expression levels. It should be noted that even three, four, five or more alternative spliced variants can be simultaneously determined using the above described method. Further, such configurations can have one, two, three, four or more alternative spliced regions which are not the same in different variants. The determined alternative spliced variants may be represented in graph form or as a regular expression or as a grammar rule. Alternatively, alternative spliced mRNA sequences are stored as a set of mRNA sequences, each of which corresponds to a single variant. Once an mRNA sequence is obtained, it is also possible to generate a real nucleotide sequence, using methods well known in the art.

In a preferred embodiment of the invention, the entire process of database reduction is repeated. ESTs which were not associated with any mRNA sequence may, at the second iteration, be associated with an mRNA sequence. Alternatively, ESTs which remain unmatched are discarded.

PROTEIN MATCHING

After the mRNA sequences are generated it is useful to compare the protein which is encoded by the sequence to an existing protein database(s). Near matches may be used to determine errors in the mRNA sequences. Such errors are preferably corrected and their effect fed back to earlier steps in the algorithm. In addition, chimeric sequences may be discovered by such a comparison. Further, alternative splices in the mRNA or in the protein database may be determined by comparing the two reduced database and the protein database. In such a case, the mRNA sequence and/or the protein database are preferably updated to include the newly discovered alternative splices. Near and exact matches are preferably associated with the reduced mRNA sequences for further use. In addition, some types of near matches and matches with protein families and/or domains can also be used to determine various functional characteristics of the protein. Further, if two clusters each match different parts of a known protein, these two clusters are preferably merged.

In a preferred embodiment of the invention, the graph of the mRNA sequence is compared as a whole to a protein database. Thus, ambiguous bases and codons can be resolved at a later date, when the graph is compared to a protein database.

In a preferred embodiment of the invention, data from different raw databases are combined by comparing the mRNA sequences and their associated proteins in the two databases, after reduction of each raw database, rather than by combining the two raw databases. Alternatively, two EST databases may be combined after clustering. Preferably, error correction is not propagated between two such databases. Alternatively, at least some of the error identification and/or correction are propagated between the databases. It should be noted that, using some of the methods described herein, it is possible to combine an EST database with an mRNA database, since ESTs are similar to mRNA sequences, only shorter. Further, some mRNA sequences have been determined from genomic databases, by identifying the introns.

In accordance with another preferred embodiment of the invention, the function of the protein encoded by the determined mRNA sequence is analyzed by finding known proteins with a similar structure. This type of analysis is especially useful to discover cells in non-human creatures which create proteins which are similar to human proteins. These types of cells are useful for studying the functioning of the protein.

GENOME MATCHING

Additionally or alternatively to matching the mRNA sequences to protein databases, the mRNA sequences may be matched to genome database(s), to find the gene from which the mRNA was transcribed. This type of matching can serve several purposes. First, some types of errors can be corrected by comparing the mRNA sequence with the source DNA. Second, by comparing the mRNA with the source DNA, the mechanism of alternative splicing, especially or the particular mRNA sequence, may be determined. Third, this comparison can serve as a diagnostic tool by identifying critical mutations. For example, certain types of cancer are caused by mutations in the DNA. Such mutations will generally causes changes in the transcription of the mRNA, which can be determined by comparing the mRNA against a baseline database, such as the human genome project database.

INTEGRATION WITH DATABASE INFORMATION

One aspect of some embodiments of the present invention relates to integrating information in the raw database with the process of clustering, assembly an error correction and/or identification. In accordance with one preferred embodiment of the invention, the clustering, assembly and/ or error correction and identification are tested against the database information to determine the possibility of errors. Such errors are preferably fed back to earlier steps in the process. Alternatively or additionally, the raw database information is integrated into the above-described processed. One example of integration is that the probability of two ESTs belonging to the same cluster increases if they are from the same tissue type. Another example of integration is that if two ESTs have similar expression levels there is a higher probability that they are associated (and vice-versa).

In a preferred embodiment of the invention, each EST has associated therewith the probabilities of correct identification and/or of misidentification of bases in the particular EST during the EST readout. Alternatively or additionally, the raw database includes statistical ranges for acquisition parameters, from which probability of various error types may be determined.

In a preferred embodiment of the invention, the EST database preferably includes one or more of the following items of information, inter alia, the following information: tissue type, cDNA library origin, clone name, expression level and chromosome association. Being from the same clone and/or from the same chromosome preferably increases the probability of two ESTs belonging to the same cluster.

VARIATIONS AND CAVEATS

In some cases, an EST which exists in the database is the complement of a correct EST. In a preferred embodiment of the invention, ESTs are entered both in their original form and as their complements. Alternatively, each time two ESTs are matched or other reference is made to the base sequences of the ESTs, provision is made for the complement, such as by generating an index of both the original EST and its complement.

It should be appreciated that the above described methods can be applied directly to chromatograms. It should be noted that by directly analyzing the chromatograms it is possible to determine various error probabilities, such as the probability of mis-identifying a particular base.

It should be noted that even though this process is especially adapted for removing redundancy and generating mRNA sequences in an entire database, it may also be used to compare a single EST with a database. In a preferred embodiment of the invention, the n-group index of the database is stored with the database, to facilitate such matching. In addition, such an indexed database is easier to combine with a second database, since the clustering is easier and faster to update.

One important issue in tuning the algorithm is determining how to apply limitations to the reduction process. If the reduction process is too strict, the process might fail, since the biological data involved has many errors. However, if the process is too lax, the reduction ratio will be small and many of the associations will be mistaken. In some preferred embodiments of the invention, most limitations are applied at later stages and then fed back to previous stages. Alternatively, a more strict process may be used, where if the results are not sufficient, the feedback to earlier steps makes them less strict, by removing previously applied limitations. Alternatively, a more lenient process may be used, where if the results are not sufficient, the feedback to earlier steps makes them more strict, by adding limitations.

There are many places in the above described database reduction method where there is a wide latitude for applying limitations, for example, by changing decision parameters. A most important such place is in associating an EST with a cluster. Rather than a binary description, it is possible to use a fuzzy-logic type description of an EST belonging to a cluster. Additionally or alternatively, a grade may be assigned to each association of an EST with a cluster, based on feedback from other steps, database information, such as tissue type and/or expression level. In one example, the grade of a matching of an EST to a cluster is dependent on the number of matching n-groups and on the required spacing between the n-groups in the particular EST.

It should be appreciated that every time a correction is made to the ESTs, there is a possibility that the correction should not be made or that a different correction should be made. In a preferred embodiment of the invention, an expert system is used to decide whether to apply a correction. One input to such a system are apriori probabilities of different types of errors and/or of possible corrections to certain types of errors. Another input is feedback from later stages of the algorithm, at which an apostriori probability for these errors can be generated, for a particular database and/or EST. In addition, the feedback can contain information about the correctness of correcting particular errors. For example, at an earlier stage, a base is deemed to be missing from an EST, so, a new base is inserted at a particular location. In a later stage, such as assembly, it is determined that the assumed location of the missing base was not correct. Not only can the proper correction be made, but, preferably, the clustering is performed again, since by adding or removing a base, the matching of n-groups may be changed.

It should be appreciated that performing the clustering again is not a difficult task, since, in most cases, the existing indexes need to be only slightly modified. In addition, it is possible to update only the clustering of the ESTs which had high grades of matching.

In a preferred embodiment of the invention, the output of the process includes a certainty value for each assembled mRNA, and, preferably, also for each correction on the assembled mRNA sequences. This value is preferably bases on the above described grades and/or on a comparison with protein databases and genome databases.

It should be appreciated that the above described order of application of steps is not required for the operation of the reduction method, rather, the above described order is varied in preferred embodiments of the invention. In one example, error correction is applied after clustering. In another example, comparing to genome databases is performed before clustering, to assist clustering. Error correction in particular may be performed at many different times during the process, since information necessary to identify and/or correct errors is continually being collected and./or updates as the process progresses.

The above-described process has been described as a combination of many features, decision parameters and probabilities. It should be appreciated that not all of these above-described features, decision parameters and/or probabilities are utilized in all preferred embodiments of the invention.

In accordance with a preferred embodiment of the invention, the above described process is embodied in a general purpose computer running software. Such software may be provided on a computer readable media, such as a diskette or a tape. Alternatively, some of the software is run on a Bioccelerator, available from Compugen Ltd. of Petach Tikva, Israel.

Attached herein as an appendix "A" is software suitable for performing some of the above-described preferred embodiments of the invention. It should be noted that this software is provided prior to integration thereof, so that various bugs in the program may exist. In particular, these are provided scripts which convert data from formats suitable for one module of the program to a format suitable for other modules. In the current state of the supplied software, the software is suitable for application as a set of tools, which may be manually applied to perform various steps of some the above described methods.

An important aspect of using an automated algorithm to correct errors and/or sequence mRNA sequences from EST database is the fine-tuning of various parameters therein. In particular, in the present algorithm, the size of n-groups, the number of n-group matches needed to associate two ESTs, the method of grading an association of an EST to a database, the probability level at which a base is assumed to be correctly identified, the weight placed on tissue type identification when associating ESTs and the allowed distance between two matching n-groups are all important parameters in various embodiments of the present invention. The values of these parameters is dependent, to some extent on the size of the database, the average size of ESTs and the type and distributions of errors in the ESTs. Typically, the above-described methods are applied in order to minimize confusion in the database. As such, one important goal is to reduce redundancy, especially by associating two ESTs and merging them together into a single mRNA sequence. Another important goal is not to create association between two ESTs which are not truly associated.

In accordance with a preferred embodiment of the invention, various parameters of the database are manually and/or automatically adjusted to maximize these goals. In one example, the set of n-groups to be ignored while indexing is automatically determined by analyzing the database. In another example, the distribution of errors is obtained by applying a first iteration of the method to the database or a portion thereof. Thus, in an iterative application, the first iteration may be considered a calibration run. In another example, the method is applied to a raw database with one set of values for various parameters. If the resulting compression and/or data quality are insufficient, the set of values are changed and the method is re-applied. Preferably, search methods, well known in the art, are used to guide the modification of the set of values.

It should be appreciated that automatic calibration is especially important in a medical laboratory setting, where a large number of samples are to be analyzed by a single machine. In such settings, an expert who knows how to adjust the device will generally not be available. Further, a great variability between the samples, especially with regard to size and error types may also be expected.

It should be appreciated that the above described process of database reduction comprises several distinct steps and ideas, some of these ideas can be practiced in isolation from other ideas, in some preferred embodiments of the invention. Alternatively or additionally, various steps in the process may be replaced by equivalent steps which are known in the art, without affecting the spirit of some embodiments of the present invention.

It should be appreciated that some of the steps described above may be used as stand-alone modules for other tasks. For example, the method of indexing EST to facilitate clustering is also useful for searching DNA databases. In addition, application of set-operators, such as intersection, union and difference on two indexed databases is much faster than on non-indexed database. Typically, a first step in applying such operators is to identify which ESTs are similar in the two databases. A large percentage of the similar ESTs are indexed under similar n-groups. Thus, a reasonably good intersection between databases can be obtained by comparing only ESTs which are indexed using the same (or mostly the same, as some errors are to be expected) n-groups.

APPLICATIONS

In the present art of mRNA analysis, the portion of the task between obtaining the tissue sample and reading out the ESTs requires only time, patience and a skilled technician. However, Once the ESTs are gathered, combining them to form correct mRNA sequences requires an expert with extensive experience and superior abilities. In addition, even once the mRNA sequences are determined, many are incomplete or incorrect since they do not take into account the possibility of alternative splicing.

In accordance with a preferred embodiment of the invention, there is no need for an expert individual to create the mRNA sequences. Rather, the generation of mRNA sequences from ESTs is made more simple and more automatic.

In accordance with a preferred embodiment of the invention, diseases are diagnosed by mRNA analysis, without the need for a highly qualified person to aid in mRNA assembly. A sample of tissue to be analyzed is removed from a patient's body. This tissue is then processed to produce ESTs. The ESTs are inputted into a device in accordance with a preferred embodiment of the invention and a spectrum of mRNA in the tissue sample is generated. This spectrum can be automatically compared to known spectra of diseases, such as cancer, to determine the existence and type of cancer. In addition, the spectrum can be analyzed to determine the instant function of the cells in the tissue sample (healthy cells, stressed cells and ill cells all express different proteins). Such analysis may be automatic, by comparing the measured spectrum against a standard and/or patient base line. Further, the spectrum can be analyzed against known pathogens, such as bacteria, viruses, funguses and other parasites, to determine the existence and type of pathogen in the body. Further, prion infections can be detected by determining an increases production of certain types of proteins, to replace those damaged by the prions. In accordance with a preferred embodiment of the invention, EST determination is also automated by incorporating a DNA chip into the diagnosis device. The biological sample is then more directly inputted into the diagnosis device.

It should be appreciated that the above-described method of database reduction is especially suitable for use with DNA chips, since the method works well even with short nucleotide sequences, which are what DNA chips are usually set to detect.

The automatic determination of alternative spliced regions and variants adds another dimension to the mRNA spectrum. Instead of comparing only the relative amounts of certain types of mRNA, it is also possible to compare the changes in the distributions of the alternative spliced variants (the ratio between protein types). It is hypothesized that the alternative splice regions are differentially transcribed as a function of stresses and diseases of the cell. In accordance with a preferred embodiment of the invention, cell activity is diagnosed by differential analysis of alternative spliced variant distribution in a single tissue type. Preferably alternative splicing spectra are maintained for a plurality of tissue types, diseases and/or pathogens.

In accordance with a preferred embodiment of the invention, the mRNA assembly technique described herein is used for research purposes. One important type of research is using the mRNA sequences as drug leads. The mRNA sequences may describe whole new genes or they may be useful to as probes for detecting new genes. The new genes may also be used for screening purposes, for example to develop and/or discover useful pharmaceuticals and/or to detect genetic diseases and/or detect pathogens which include the mRNA sequence. Also, the mRNA sequences may encode proteins which have various uses, for example as pharmaceuticals. Also, the mRNA sequences themselves may be useful, for example as antisense molecules and/or as part of gene-therapy. Since the number of mRNA sequences generated by preferred embodiments of the invention are much fewer than the original number of ESTs, the number of leads which are generated is much reduced, allowing a more focused drug search. In addition, by using a process in accordance with some preferred embodiments of the present invention, the resulting mRNA sequences are longer and containing fewer errors, so a significant amount of laboratory work can be avoided. Further, some laboratory work is avoided by providing protein information derived by matching the mRNA sequences to protein domain and/or family databases.

In accordance with another preferred embodiment of the invention, the mRNA sequence with alternative splicing is compared to the originating genome, to more exactly determine the alternative spliced regions. By such comparison is it possible to correct errors in the identification of alternative spliced regions, since alternative spliced regions are usually contained and/or delimited by introns in the DNA. The originating genome for the mRNA sequence can be more correctly determined using a mRNA sequence than by using only an EST. Further, the identification of alternative spliced regions assists the search task, by indicating where a break in the correspondence may be expected. In addition, if such a search results in more than one site for a certain mRNA sequence, this result is more dependable than when multiple sites are found using ESTs. It is hoped that by comparing mRNA sequences with alternative spliced variants to DNA sequences, the mechanism of alternative splicing will be deciphered.

In accordance with a preferred embodiment of the invention, a DNA chip is designed to detect differences in the relative expression levels of alternative spliced variants of a single mRNA sequence. Such a DNA chip may be designed by first applying the above described methodology to an EST database to determine alternative spliced regions which may be of interest and then designing a DNA chip which detects all the different variants. Diagnosis can then proceed by comparing the relative expression levels with known spectra of different tissue types and/or diseases and/or by detecting changes in the spectra which may be associated with disease and/or certain types of stress.

In accordance with another preferred embodiment of the invention, a DNA chip is designed responsive to the relative distribution of short mRNA sequences in the database. Once the database is reduced to mRNA sequences, using above-described processes, a minimum number of short DNA sequences, which uniquely identify a maximum number of mRNA sequences, is preferably determined. These methods are not useful on EST databases, since there is too much redundancy and too many errors to guarantee a usable subset. Alternatively, the DNA sequences may be selected to generate a minimum error level during identification of a particular group of mRNA sequences. Alternatively, identification of a maximum number of mRNA sequences is the goal. Alternatively, identification of a certain subset of mRNA sequences is the goal. The mRNA sequences to be identified may be selected based on differential analysis and or based on genomic and/or mRNA mapping of pathogens. By correctly selecting the mRNA sequences, a single DNA chip may also be used to detect a screen for a plurality of diseases.

In a preferred embodiment of the invention, DNA chip design is greatly accelerated using methods described herein. One important task required for many methodologies of DNA chip design and analysis of data, is determining an index of short sequences of DNA in a large database of mRNA sequences, ESTs or DNA sequences. As can be appreciated, the above described n-group indexing method for clustering may be used for this purpose. Further, by repeating applying an n-group indexing (preferably without any limitation on distance between n-groups), the mRNA sequences are divided into lists. A list which contains only one mRNA indicates that that mRNA sequence can be uniquely identified using only the n-groups which identify that list. The fewer reindexings needed, the smaller the number of n-groups needed to uniquely identify the mRNA or DNA sequence. Preferably, n is between 10 and 50, more preferably, between 20 and 30, most preferably, about 25.

In another example, DNA chip design may require that a probe for a genomic data base does not appear in a second database. I.e., a probe for a disease pathogen should not "detect" a naturally expressed mRNA sequence. Also, some sets of probes are more suitable and/or may be more effectively manufactured in a DNA chip setting. In a preferred embodiment of the invention, a the indexing may be utilized to determine not only that a probe is unique but also a uniqueness score. The probes may then be sorted in order of uniqueness and the selection of appropriate probes or sets of probes may start from the top of the list. The uniqueness of a probe may be defined as a function of relative expression levels and the number and/or location of mismatched nucleotides between a probe and an existing EST portion. The above indexing method provides, as a side effect, locations of EST portions which are similar to the probe, i.e., where one, two or more n-groups match. For each probe, it is possible to analyze the indexes of n-groups which appear in the probe to determine a score for the probe. It should be noted that even if the score is not precise and some EST portions are missed for a particular probe, this may be compensated for by selecting more than one probe for a particular mRNA sequence. Also, once a probe is selected, the probe may be separately analyzed to determine if its uniqueness is sufficient. In a preferred embodiment of the invention, the uniqueness score of a probe is used when analyzing the results of a DNA chip. Thus, each probe on a DNA chip may be separately evaluated to yield an individual false positive/false negative probability, based, for example, on known or assumed concentrations of nucleotide sequences and/or know affinities of such nucleotide sequences to the probes used.

Another "side effect" of the above described clustering algorithm is the detection of SNPs (Single Nucleotide Polymorphisms). If, for example, ten ESTs overlap and five have one nucleotide at a certain position and five have a second nucleotide at the corresponding position, the different nucleotide is a candidate SNP. Preferably the determination if a single nucleotide difference is also a useful SNP, is dependent on statistical considerations, which are preferably an input to the system. Such considerations may include the number of overlapping. ESTs the number of ESTs in which each variant appears, the probability of errors in sequencing and/or the effect of the difference on a protein encoded by the sequence. In a preferred embodiment of the invention, probes for the SNPs are grouped together to form an assay of SNPs useful for genetic mapping. Preferably, a large set of probes is manufactured on a DNA chip. In a preferred embodiment of the invention, the above described methods of determining a uniqueness of a probe are also used to determine the uniqueness of SNP probes.

It should be appreciated that this method of n-group indexing is also useful for other methods of DNA detection which utilize the identification of short DNA sequences to uniquely identify certain genes or mRNA sequences.

EXAMPLES

Discussed below are transcript listings of mRNA sequences and clusters of ESTs, which were generated from a public domain database of a mouse, in accordance with preferred embodiments of the present invention. There are three cluster descriptions, each having the following format:

(a) a short description of the cluster;
(b) a list of the mRNA sequences and the associated ESTs used to generate the sequences;
(c) for each EST alternative spliced variant, a cross-reference listing between the sequence and a consensus of all the ESTs;
(d) a sequence listing of the consensus of all the ESTs, which need not match any particular variant; and
(e) transcriptions of the alternative spliced variants detected for the mRNA sequence.

For example, sequence number 10827, contains two transcripts, one corresponding to each of the two alternative spliced variants.

The cross-reference listing shows gaps in the sequence for the 10827_0 variant. These gaps correspond to alternative spliced regions which are part of the 10827_1 variant.

In a preferred embodiment of the invention, alternative spliced regions which correspond to graph nodes are displayed using a different color, so that they stand out on a graphical display.

The sequence 15537, contains only one variant.

The sequence 19101, contains four alternative spliced variants, only two of which are transcribed, the rest shown only as part of cross-referencing against the consensus sequence. Additional transcripts of mRNA sequences are in Israel patent application 121,806, filed Sep. 21, 1997, the disclosure of which is incorporated herein by reference.

In accordance with a preferred embodiment of the invention, a DNA chip is designated to differently recognized a particular variant by including in the DNA chip sensor array only those n-groups (where n is preferably 25) which appear only in one variant but not in the other. There is also provided in accordance with a preferred embodiment of the invention, a kit of short DNA sequences, determined from such an analysis of mRNA expression.

It will be appreciated by a person skilled in the art that the present invention is not limited by what has thus far been described. Rather, the present invention is limited only by the claims which follow.

What is claimed is:

1. A method for clustering ESTs, comprising:
   (a) for each of one or more n-groups,
      (aa) associating with the n-group a list of ESTs from among a plurality of ESTs, each EST on the list containing the n-group; and
      (ab) matching ESTs on the list to generate a cluster.

2. The method of claim 1, wherein associating a list with an n-group comprises associating with the n-group a list of ESTs from among the plurality of ESTs, each EST on the list containing the n-group and further containing at least one other predetermined n-group.

3. The method of claim 2, wherein each EST on a list further contains a second predetermined n-group.

4. The method of claim 3, wherein each EST on a list further contains a third predetermined n-group.

5. The method of claim 4, wherein each EST on the list further fourth predetermined n-group.

6. The method of claim 2, wherein for each EST on the list, a first specified n-group is distanced from a second specified n-group less than a predetermined number of bases.

7. The method of claim 6, wherein the predetermined number of bases is less than five.

8. The method of claim 7, wherein the predetermined number of bases is less than four.

9. The method of claim 8, wherein the predetermined number of bases is less than three.

10. The method of claim 1, wherein matching ESTs comprises correlating ESTs on a list using an SW (Smith-Waterman) algorithm.

11. The method of claim 1, wherein matching ESTs comprises correlating said ESTs using an SW (Smith-Waterman) algorithm modified to include detection of long gaps.

12. The method of claim 1, wherein the n-groups are between 5 and 15 bases long.

13. The method of claim 12, wherein the n-groups are 9 bases long.

14. The method of claim 1, further comprising:
   (a) assembling the clustered ESTs;
   (b) detecting errors in the ESTs based upon the assembling; and
   (c) rematching the list of ESTs based upon detected errors.

* * * * *